United States Patent
Fix et al.

(10) Patent No.: US 9,587,968 B2
(45) Date of Patent: Mar. 7, 2017

(54) SENSOR DEVICE AND METHOD FOR PRODUCING A SENSOR DEVICE

(71) Applicant: Robert Bosch GmbH, Stuttgart (DE)

(72) Inventors: Richard Fix, Gerlingen (DE); Andreas Krauss, Tuebingen (DE)

(73) Assignee: Robert Bosch GmbH, Stuttgart (DE)

( * ) Notice: Subject to any disclaimer, the term of this patent is extended or adjusted under 35 U.S.C. 154(b) by 192 days.

(21) Appl. No.: 14/217,591

(22) Filed: Mar. 18, 2014

(65) Prior Publication Data
US 2014/0283632 A1    Sep. 25, 2014

(30) Foreign Application Priority Data

Mar. 19, 2013 (DE) .................. 10 2013 204 804

(51) Int. Cl.
*G01N 27/00* (2006.01)
*G01D 11/30* (2006.01)
*G01N 27/414* (2006.01)

(52) U.S. Cl.
CPC ............. *G01D 11/30* (2013.01); *G01N 27/00* (2013.01); *G01N 27/414* (2013.01)

(58) Field of Classification Search
CPC ....... G01D 11/30; G01N 27/00; G01N 27/414
See application file for complete search history.

(56) References Cited

U.S. PATENT DOCUMENTS

| 5,652,384 A * | 7/1997 | Henrion ............... G01P 15/02 73/514.18 |
| 2006/0081227 A1* | 4/2006 | Nonaka ............... F01N 13/008 123/568.11 |
| 2010/0207602 A1* | 8/2010 | Loverich ............. G01N 29/022 324/76.49 |

FOREIGN PATENT DOCUMENTS

| DE | 10 2008 008 535 A1 | 8/2009 |
| DE | 10 2010 031 153 A1 | 1/2012 |

* cited by examiner

*Primary Examiner* — Paul West
(74) *Attorney, Agent, or Firm* — Maginot, Moore & Beck LLP

(57) ABSTRACT

A sensor device includes a sensor element configured to detect a measurement value based at least in part upon a physical variable, and a support element configured to support the sensor element. The support element has at least one connection region which is located in a section of the support element, and which is configured to connect the section of the support element to a section of the sensor element such that the sensor element is mounted so as to be movable with respect to the support element.

12 Claims, 2 Drawing Sheets

SENSOR DEVICE AND METHOD FOR PRODUCING A SENSOR DEVICE

This application claims priority under 35 U.S.C. §119 to patent application no. DE 10 2013 204 804.1, filed on Mar. 19, 2013 in Germany, the disclosure of which is incorporated herein by reference in its entirety.

The present disclosure relates to a sensor device and to a method for producing a sensor device.

BACKGROUND

For the fixing of sensor elements, for example of semiconductor-based gas sensors which are composed in particular of silicon carbide, it is necessary, in particular where these are to be used as exhaust-gas sensors, to realize resistance to elevated operating temperatures (up to 500° C.) and to other harsh ambient conditions (moisture, gases, etc.). It is therefore not possible here, owing to the high temperatures, to use the conventional organic adhesives such as are used in electronics manufacturing with silicon semiconductor die and on printed circuit boards or LTCC ceramic material.

Sensor elements may for example be chemical sensors such as ChemFETs, MECS sensors or other sensors that detect physical variables. These are normally realized using high-temperature-resistant materials, for example silicon carbide. Said material, owing to its coefficient of thermal expansion, cannot be combined with conventional standard materials in situations involving fluctuating temperatures.

DE 10 2008 008 535 A1 relates to a device for the fixing and/or fastening of an electronic module, such as a semiconductor element, and the electrically conductive connection thereof to conductor paths on a support, by way of a fixing element or fixing means. The fixing element or means is designed so as to maintain its fixing characteristics at operating temperatures of up to 500° C.

SUMMARY

Against this background, the present disclosure proposes a sensor device and a method for producing a sensor device. Advantageous refinements will emerge from the claims and the following description.

To address the problem described in the introduction, possible approaches are to change the conventional construction and to use special high-temperature-resistant adhesives and substrates that are matched in terms of coefficients of thermal expansion.

A punctiform fastening, proposed herein, of a sensor element to a support element makes it possible to realize a robust sensor device in which the sensor element and the support element have different coefficients of thermal expansion.

With the approach proposed here, it is for example possible for a support formed from silicon to be used for the fixing of a sensor element, in particular a semiconductor-based sensor, composed for example of silicon carbide, silicon or gallium nitride. In particular, it is possible here for a structuring of connection elements or regions between support and sensor element to be designed such that a mechanical movement of the components relative to one another is possible, and thus different materials with different coefficients of thermal expansion can be durably connected to one another. In one refinement of the concept proposed here, the support or the support element may be structurable or structured by means of methods from microsystem technology.

An advantage of the concept proposed here is that, in the event of a thermal expansion, no mechanical stresses, or only limited mechanical stresses, are generated between the constituent parts of a sensor designed in this way, such that fatigue-free operation is possible under fluctuating temperatures.

With the approach proposed here, it is possible for a gas sensor to be provided which can withstand high temperatures, which is in particular resistant to temperature fluctuations, and in the case of which it is possible to dispense with the use of special materials or measures that require high outlay and which would increase the spatial requirement for example owing to restrictions in minimum conductor path width, contact area or conductor path spacing.

A sensor device has the following features:
a sensor element for detecting a measurement value on the basis of a physical variable; and
a support element for supporting the sensor element, wherein the support element has at least one connection region which is arranged in a section of the support element and which is designed to connect the section of the support element to a section of the sensor element such that the sensor element is mounted so as to be movable with respect to the support element.

The sensor device may for example be used for the detection and analysis of gases, for example in the exhaust tract of a vehicle, and may correspondingly have material characteristics that permit reliable operation of the sensor device at high temperatures. The sensor element may for example be produced from silicon carbide or some other semiconductor material that can withstand high temperatures, and may be positioned so as to be exposed to one or more gases directly, or in a definedly restricted form, in order to be able to detect the measurement value. The sensor element may be of flat rectangular form. The support element may likewise substantially be of flat rectangular form and may be formed for example from silicon, ceramic or some other inexpensive material that can withstand high temperatures. The support element may be designed firstly to fix the sensor element by means of the at least one connection region and secondly to expose said sensor element in an optimum manner to the gas to be analysed. The support element may for example have two such connection regions spaced apart from one another. The section of the support element and the section of the sensor element may in each case be a small sub-region, or small sub-regions spaced apart from one another, of a respective side surface of the support element and of the sensor element respectively. The connection region may be designed to connect the sensor element to the support element in non-positively locking and/or positively locking fashion. The connection region may furthermore be designed such that physical contact between the support element and the sensor element is restricted to the connection region. In this way, the sensor element can be exposed over its full extent, aside from a section connected to the connection region, to a gas flow. Likewise as a result of the reduced contact region in the form of the connection region, a temperature difference between the support element and sensor element may either be possible or realized in a targeted manner, for example through active heating of only the sensor element, because only a reduced amount of heat is transmitted via the connection region. The mounting of the sensor element relative to the support element may be configured such that the sensor element is movable transversely and/or in parallel and/or obliquely with respect to a main direction of extent of the support element, wherein the main direction of extent can be understood as running along a largest surface of the support element.

In one embodiment of the sensor device, the connection region may be in the form of a flexible web, arranged in a recess of the support element, for the resilient mounting of the sensor element. Here, a first end of the flexible web may be cohesively connected to the section of the support element, and a second end of the flexible web may be cohesively connected to the section of the sensor element. The flexible web may be a constituent part of the support element, and may be formed for example in an etching process by removal of material of the support element. Owing to the resilient mounting, an oscillation of the sensor element can be permitted to a predetermined extent, such that the sensor element can be designed to be robust with respect to vibrations or shocks, for example. The sensor element may for example have two or more such flexible webs. The recess may be arranged in a main side of the rectangular support element, wherein a main side can be understood to be one of two opposite side surfaces, which are the largest in terms of area, of the support element. The one or more flexible webs may in this case be arranged such that a main side of the sensor element, which may have modules required for the detection of the measurement value, is situated opposite the recess. The main side of the sensor element may be understood to be one of two opposite side surfaces, which are the largest in terms of area, of the sensor element. Owing to this arrangement, it is advantageously possible for a cavity to be formed between the support element and sensor element, into which cavity the gas to be analysed can be conducted. It is thus possible for the measurement to be performed in a highly direct and thus more accurate manner.

In particular, the flexible web may be assembled from a first web part, which has the first end, and a second web part, which has the second end and which runs at an angle, of greater than 0° and less than 180°, with respect to the first web part. The section of the support element may be part of a side wall of the recess, and the section of the sensor element may be part of a main surface, facing toward the recess, of the sensor element. Here, the main surface of the sensor element may be larger than the recess, such that an edge region of the main surface of the sensor element is situated opposite a border region, which surrounds the recess, of the support element. This embodiment makes it possible to realize the resilient mounting of the sensor element in a simple and inexpensive manner. The sensor device is thus even more robust with respect to shocks and vibrations.

It is for example possible for the first web part to extend substantially parallel to the main surface of the sensor element and for the second web part to extend substantially parallel to the side wall of the recess. With this embodiment, it is possible to realize a design of the flexible web which is particularly simple to produce.

Furthermore, the first web part may have an angled or curved profile. This embodiment offers the advantage that the flexible web can exhibit greater resistance to breakage.

In a further embodiment, the connection region may have at least one electrical terminal for the electrical contacting between the sensor element and the support element. It is thus advantageously possible for the electrical contacting to be realized in a space-saving and electrically insulated manner.

In particular, physical contact between the sensor element and the support element may be restricted to the connection region. It is thus possible to realize advantageous thermal insulation of the sensor element with respect to the support element.

In a further embodiment, the connection region may be designed such that, by exerting a preload, it holds or presses the sensor element against a surface of the support element surrounding the recess of the support element, and forms a closed cavity in the recess. Such a closed, fluid-tight or approximately fluid-tight cavity can advantageously be used as a reference air reservoir.

Furthermore, the support element may have a multiplicity of electrically insulated conductor paths for the electrical contacting of the sensor device. Furthermore, the support element may have a passivation layer which at least partially covers the conductor paths. This embodiment permits simple rewiring for the connection of additional modules to the support element at suitable positions in a manner dependent on the desired specification. It is thus advantageously possible for the sensor device to be readily adapted to a wide variety of applications.

In particular, the support element may be manufactured using microstructure technology. It is thus advantageously possible for the sensor device to be realized with a small structural size.

A method for producing a sensor device has the following steps:

providing a sensor element for detecting a measurement value on the basis of a physical variable; and providing a support element for supporting the sensor element, wherein the support element has at least one connection region which is arranged in a section of the support element;

connecting the connection region to a section of the sensor element in order to mount the sensor element so as to be movable with respect to the support element.

In the connecting step, the sensor element may be connected to the support element in cohesive and/or non-positively locking fashion.

In one embodiment of the method, the connecting step may be performed using a die bonding method. This offers the possibility of a connection which is technically particularly simple to apply and which is simultaneously robust.

BRIEF DESCRIPTION OF THE DRAWINGS

The disclosure will be explained in more detail below, by way of an example, on the basis of the appended drawings, in which.

DETAILED DESCRIPTION

In the following description of preferred exemplary implementations of the present disclosure, elements of similar action illustrated in the various figures will be denoted by identical or similar reference signs, wherein a repeated description of said elements will not be given.

Figure 1A:
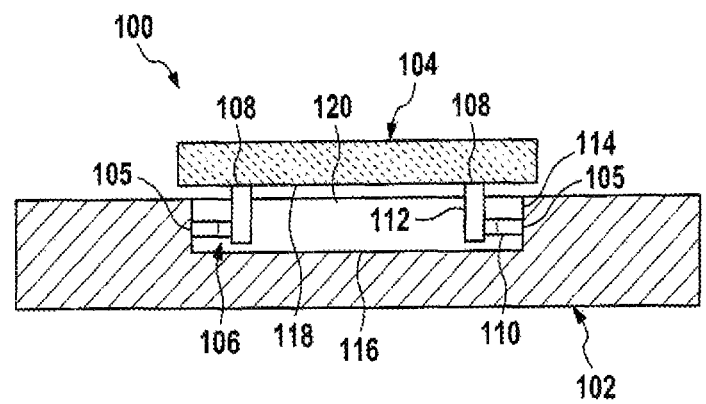
FIG. 1A is a sectional illustration of a sensor device according to an exemplary implementation of the present disclosure.

FIG. 1A shows, on the basis of a sectional illustration, an exemplary implementation of a sensor device 100. The sensor device 100 is assembled from a rectangular support or support element 102 and a likewise rectangular sensor element 104, which is however of smaller dimensions. The support element 102 is microstructured and has, in this case, two connection regions 106 which extend from two sections 105 of the support element 102, by means of which connection regions the sensor element 104 is cohesively connected, at sections 108 of the sensor element 104, to the support element 102. Correspondingly, the sections 108 of the sensor element 104 are also referred to as contact points. In this case, the connection regions 106 are in the form of flexible webs which permit resilient mounting of the sensor element 104 with respect to the support element 102. As shown by the illustration in FIG. 1A, the flexible webs 106 are in each case assembled from a first web part 110 and a second web part 112, which runs at right angles with respect to the first web part 110. The webs 106 are in this case of integral form, and have in this case been formed out of the material of the support 102 by means of an etching process. It can be seen from FIG. 1A that the connection regions 106, in the form of the flexible webs, extend from side walls 114 of a recess 116 arranged in the support element 102. By means of the connecting regions 106, the sensor element 104 is mounted relative to the support element 102 such that a main surface 118 of the sensor element 104 faces toward the recess 116. The illustration in FIG. 1 shows that the main surface 118 of the sensor element 104 is larger than the recess 116, and thus an edge region of the main surface 118 of the sensor element 104 is situated opposite a border region, which surrounds the recess 116, of the support element 102. It can however also be clearly seen from the illustration of FIG. 1A that physical contact between the support element 102 and the sensor element 104 of the sensor device 100 is restricted to the contact points 108. The sensor element 104 can thus be regarded as being mechanically decoupled from the support substrate or support element 102. A spacing between the first web parts 110 of the flexible webs 106 and a base region of the recess 116 permits the resilient mounting of the sensor element 104.

Figure 1B:
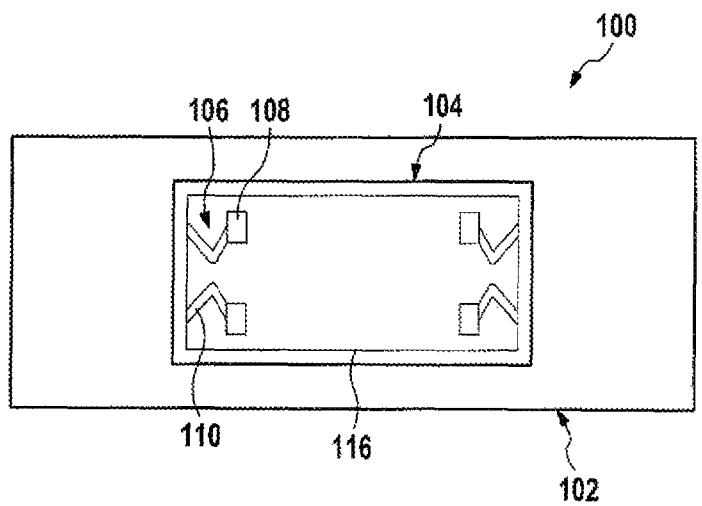
FIG. 1B is a plan view of the sensor device from FIG. 1A.

FIG. 1B shows a plan view of the sensor device 100 from FIG. 1A. In the exemplary implementation of the sensor device 100 shown here, the sensor element 104 is formed from silicon carbide and is thus partly transparent. This means that, in this perspective, it is also possible to see those regions of the support element 102 which are covered by the sensor element 104. The illustration in FIG. 1B thus shows that the respective first web parts 110 of the flexible webs 106 are of angled form, and that the respective second web parts 112 of the flexible webs are of straight form and run vertically, that is to say parallel or substantially parallel to the side walls of the recess 116, and are thus represented in this illustration by the contact points 108.

The sensor device 100 shown in FIGS. 1A and 1B may be arranged in an exhaust tract of a vehicle for exhaust-gas analysis purposes. The sensor element 104 consists in a small and thus inexpensive die. The sensor element 104 is formed from silicon carbide as a semiconductor material that can withstand high temperatures, and is equipped with one or more actual sensor components, for example with one or more chemically sensitive sensors such as ChemFETs or MECS sensors, with sensors for other physical variables if appropriate, and additionally with integrated electronics. By way of the connection regions 106, the sensor element 104 is connected to the "microstructured support" as the support element 102, the latter being formed from inexpensive microstructured material, for example from silicon, ceramic, filled or unfilled polymers, or metals. The silicon component 102 is used not as a semiconductor—the operating or ambient temperatures would be too high for it to function as a semiconductor—but merely as a microstructured mechanical support. Conductor paths which are insulated with respect to one another and with respect to the surroundings, and which are composed for example of high-temperature-resistant high-grade metals such as Pt, for example, may be applied to the support element 102 under a combined passivation layer, which permits rewiring. The support 102 may be designed or installed such that only one part is exposed to the high temperatures and the hot exhaust gas, such that, on another part of the support 102 which is at lower temperatures, it is for example possible for lines to be connected by way of conventional soldering processes or by means of plug connectors that can withstand only low temperatures. On this part of the support 102 which is at relatively low temperatures, it is also possible for further electronic circuits to be integrated in or on the support 102 if appropriate.

It is crucial that the connection between the silicon support 102 and the sensor element 106 is realized in non-positively locking and/or cohesive fashion only at the few points 108. It is also possible for in each case one or more electrical connections between the sensor element 104 and support 102 to be realized at said mechanical connection points 108. In the present case, in which silicon carbide is used as a transparent material for the sensor element 104, the alignment between the sensor 104 and support 102 can be performed in a very simple manner, because the contact points 108 of the microstructured support 102 are visible.

The connection elements 106 on the microstructured support 102 are preferably, as shown in FIGS. 1A and 1B, designed with resilient action with respect to the sensor element 104, said connection elements in this case being thin flexible webs. What are particularly advantageous—as likewise shown in FIGS. 1A and 1B—are first web parts 110 that have single or multiple bends or are curved. This suspension of the sensor 104 serves to protect the latter against mechanical influences in particular under adverse conditions, that is to say in the harsh environment such as prevails for example in the exhaust tract of a vehicle, in particular if the sensor element 104 has integrated thereon further sensors which also detect physical characteristics, for example pressure, flow speeds or the like. The merely punctiform suspension also yields thermal insulation, which can be utilized for the purpose of heating only the sensor element 104, for example to a constant or targetedly modulated temperature, with low power.

The exemplary implementation of the sensor device 100 shown in FIGS. 1A and 1B is constructed such that there is a spacing between the surface or main surface 118 of the sensor 104 and the microstructured support 102. A cavity 102 thus formed can be utilized as a gas inlet between the sensor element 104 and the microstructured support 102, such that the active surface or main surface 118 of the sensor element 104 can be oriented toward the microstructured support 102 so as to be protected against external influences. This reduces the outlay for an additional housing, or may if appropriate render such a housing entirely superfluous, and also makes it possible for the conductor paths, which are then present on the underside 118 of the sensor element 104, to be used directly as contact surfaces for the electrical connection to the microstructured support 102. Non-sensitive components, for example a heater, may be arranged on that side of the sensor element 104 which faces away from the microstructured support 102. Alternatively, in this arrangement, both sides are exposed to exhaust gas, such that sensor functions may also be implemented on both sides of the sensor element 104.

In another embodiment, not shown in the figures, of the resilient mounting 106, the latter may serve to ensure that there is no spacing or only a very small spacing between the sensor element 104 and microstructured support, for example by virtue of a preload being built up in a vertical direction, which preload pulls the sensor element 104 and support 102 together. The cavity 120 formed between the sensor element 104 and the microstructured support element 102 may then be regarded as being approximately sealed. In conjunction with a pumping cell on the sensor element 104 (not shown), a reference air reservoir can thus be generated in the cavity 120.

In a further embodiment of the sensor device 100 which is likewise not shown in the figures, the connection between the sensor element 104 and microstructured support 102 may be configured such that, at a spatially restricted location, for example at a corner or in the middle of the sensor element 104, there is a mechanically fixed connection between the sensor element 104 and the microstructured support element 102, at which multiple electrical connections may then for example also be realized. Further contact points 108 may exist at which a mechanical movement between the sensor element 104 and micromechanical support 102 is possible. Said contact points 108 are preferably realized as small, defined areas or as punctiform contact regions.

In one advantageous embodiment, the microstructured support 102 may also be realized in multiple parts; for example, a small microstructured element, which is thus inexpensive to produce, may be used as a connection between the sensor element 104 and a larger support. The larger support may then be produced in a very inexpensive manner from a conventional material, for example from ceramic or from a silicon element provided only with conductor paths as electrical connection elements.

Figure 2:
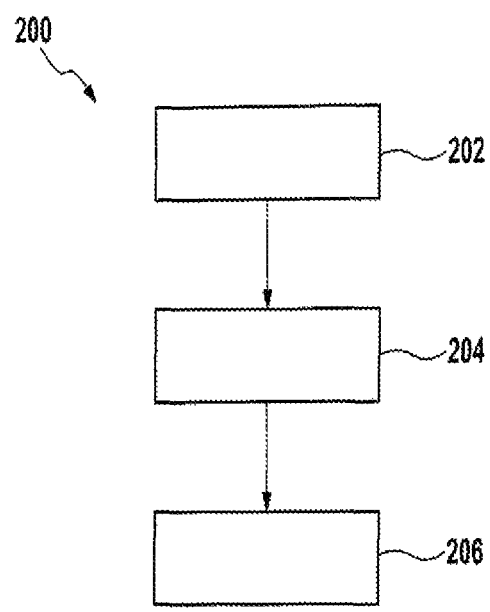
FIG. 2 is a flow diagram of a method for producing a sensor device, according to an exemplary implementation of the present disclosure.

FIG. 2 shows a flow diagram of an exemplary implementation of a method 200 for producing a sensor device. In a step 202, a sensor element for detecting a measurement value on the basis of a physical variable is provided. In a step 204, a support element for supporting the sensor element is provided. The support element is designed so as to have a connection region in at least one section. The steps 202 and 204 may be performed in parallel or in succession in any desired sequence. In a step 206, the connection region is connected to a section of the sensor element in order to mount the sensor element so as to be movable with respect to the support element. The connecting step 206 is in this case performed by means of a wafer bonding or die bonding process, for example in the form of eutectic bonding or in a silver sintering process, if appropriate also in a soldering or welding process.

The mechanical decoupling and support device, proposed herein, for sensors in the exhaust gas may for example be realized in conjunction with a ChemFET, a miniaturized lambda probe or other MECS-based gas sensors, for example NOx, HC or NH3 sensors.

The exemplary implementations described and shown in the figures have been selected merely by way of example. Different exemplary implementations may be combined with one another in their entirety or only in respect of individual features. It is also possible for one exemplary implementation to be supplemented by features of another exemplary implementation.

Furthermore, method steps according to the disclosure may be performed repeatedly and in a sequence other than that described.

Where an exemplary implementation includes an "and/or" link between a first feature and a second feature, this should be understood as meaning that the exemplary implementation has both the first feature and also the second feature in a first embodiment, and has either only the first feature or only the second feature in a further embodiment.

What is claimed is:

1. A sensor device, comprising:
a sensor element configured to detect a measurement value based at least in part upon a physical variable, wherein the sensor element is configured to detect and/or analyze gases; and
a support element configured to support the sensor element, the support element including a recess and at least two connection regions,
wherein each connection region is positioned in a respective section of the support element,
wherein each connection region is configured to connect the respective sections of the support element to respective sections of the sensor element such that the sensor element is mounted so as to be movable with respect to the support element, and
wherein each of the connection regions is positioned in the recess of the support element and the sensor element is positioned outside of the recess.

2. The sensor device according to claim 1, wherein:
each of the connection regions is a flexible web and is configured to resiliently mount the sensor element;
a first end of each of the flexible webs is cohesively connected to the respective section of the support element; and
a second end of each of the flexible webs is cohesively connected to the respective section of the sensor element.

3. The sensor device according to claim 2, wherein:
each flexible web includes:
a first web part having the first end; and
a second web part having the second end, and which runs at an angle with respect to the first web part;
each of the respective sections of the support element is part of a side wall of the recess;
each of the respective sections of the sensor element is part of a main surface of the sensor element facing toward the recess; and
the main surface is larger than the recess, such that an edge region of the main surface is positioned opposite a border region that surrounds the recess.

4. The sensor device according to claim 3, wherein:
each of the first web parts extends substantially parallel to the main surface; and
each of the second web parts extends substantially parallel to the side wall.

5. The sensor device according to claim 3, wherein each of the first web parts includes an angled profile or a curved profile.

6. The sensor device according to claim 2, wherein each of the connection regions:
is configured to press the sensor element against a surface of the support element surrounding the recess by exerting a preload; and
forms a closed cavity in the recess.

7. The sensor device according to claim 1, wherein each of the connection regions includes at least one electrical terminal configured to provide electrical contact between the sensor element and the support element.

8. The sensor device according to claim 1, wherein the sensor element only physically contacts the support element via the connection regions.

9. The sensor device according to claim 1, wherein the support element includes a plurality of electrically insulated conductor paths configured to electrically contact the sensor device.

10. The sensor device according to claim 1, wherein the support element is a microstructured support element.

11. A method of producing a sensor device, comprising:
connecting at least two connection regions of a support element to respective sections of a sensor element, such that the sensor element is mounted so as to be movable with respect to the support element, wherein:
the support element includes a recess and is configured to support the sensor element such that the sensor element is positioned outside of the recess;
each of the connection regions is located in a respective section of the support element;
the sensor element is configured to detect a measurement value based at least in part upon a physical variable;
the sensor element is configured to detect and/or analyze gases; and
each of the connection regions is positioned in the recess of the support element.

12. The method of producing a sensor device according to claim 11, wherein connecting each of the connection regions of the support element to the respective section of the sensor element includes die bonding.

* * * * *